(12) United States Patent
Bryan et al.

(10) Patent No.: US 9,792,681 B2
(45) Date of Patent: Oct. 17, 2017

(54) SYSTEM AND METHOD FOR MEDICAL IMAGE ANALYSIS AND PROBABILISTIC DIAGNOSIS

(71) Applicant: The Trustees of The University of Pennsylvania, Philadelphia, PA (US)

(72) Inventors: Robert Nicholas Bryan, Philadelphia, PA (US); Edward H. Herskovits, Baltimore, MD (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 9 days.

(21) Appl. No.: 14/784,161

(22) PCT Filed: Apr. 11, 2014

(86) PCT No.: PCT/US2014/033715
§ 371 (c)(1),
(2) Date: Oct. 13, 2015

(87) PCT Pub. No.: WO2014/169164
PCT Pub. Date: Oct. 16, 2014

(65) Prior Publication Data
US 2016/0048956 A1 Feb. 18, 2016

Related U.S. Application Data

(60) Provisional application No. 61/811,731, filed on Apr. 13, 2013, provisional application No. 61/812,112, filed on Apr. 15, 2013.

(51) Int. Cl.
*G06K 9/00* (2006.01)
*G06T 7/00* (2017.01)
(Continued)

(52) U.S. Cl.
CPC .......... *G06T 7/0012* (2013.01); *G06F 19/321* (2013.01); *G06F 19/345* (2013.01);
(Continued)

(58) Field of Classification Search
CPC .............. G06K 9/00; G06T 7/00; G06F 19/00
(Continued)

(56) References Cited

U.S. PATENT DOCUMENTS 7,333,645 B1 * 2/2008 Mitchell .............. G06K 9/3233
128/920
7,379,885 B1 * 5/2008 Zakim ................... G06F 19/322
600/300
(Continued)

*Primary Examiner* — Abolfazl Tabatabai
(74) *Attorney, Agent, or Firm* — Baker & Hostetler LLP

(57) ABSTRACT

Methods and systems for obtaining a probabilistic diagnosis based on medical images of a patient are disclosed. In exemplary embodiments, such methods include the steps of scanning some or all of a patient to obtain a medical image; evaluating the medical image for one or more designated key features; assigning discrete values to the one or more designated key features to form a patient scan key feature pattern; and transmitting the values of the one or more designated key features to a processor programmed to match the patient scan key feature pattern to one or more known disease-specific key feature patterns to create a probabilistic diagnosis and transmit the probabilistic diagnosis to a user. Associated systems include a medical imaging device that is capable of producing a medical image of some or all of a patient and a processor programmed to create a probabilistic diagnosis.

18 Claims, 6 Drawing Sheets

(51) Int. Cl.
 *G06F 19/00* (2011.01)
 *G06K 9/46* (2006.01)
 *G06K 9/52* (2006.01)
 *G06K 9/62* (2006.01)
 *G06N 7/00* (2006.01)
 *A61B 5/00* (2006.01)

(52) U.S. Cl.
 CPC ............ *G06K 9/4671* (2013.01); *G06K 9/52* (2013.01); *G06K 9/6201* (2013.01); *G06N 7/005* (2013.01); *G06T 2207/30004* (2013.01)

(58) Field of Classification Search
 USPC ............ 382/128–134; 378/4, 8, 21–27, 901; 600/407, 410, 411, 425, 427, 300
 See application file for complete search history.

(56) References Cited

U.S. PATENT DOCUMENTS

| | | |
|---|---|---|
| 2004/0086162 A1 | 5/2004 | Doi et al. |
| 2007/0133852 A1 | 6/2007 | Collins et al. |
| 2008/0104116 A1 | 5/2008 | Van Hoe et al. |
| 2010/0266179 A1 | 10/2010 | Ramsay et al. |
| 2011/0166879 A1* | 7/2011 | Lee .................... G06F 19/3443 705/2 |
| 2011/0243417 A1 | 10/2011 | Madabhushi et al. |

\* cited by examiner

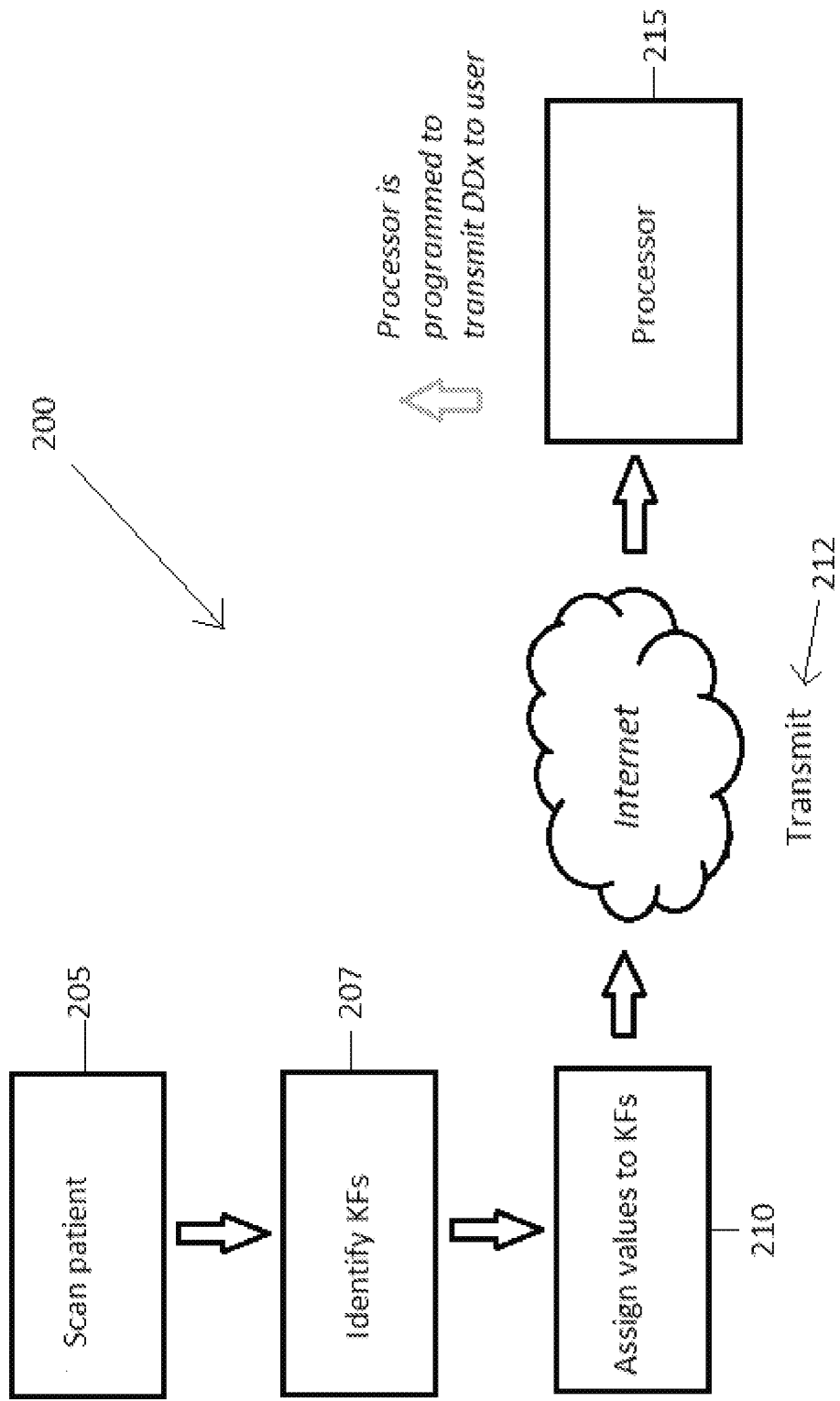

| RNB | SIGNAL | | | | | | | | | | | | | | | T2* | | SPACE | | | | | | | | | | | | | | | PRIOR | | |
| | T1 | | | Post T1 | | | T2 | | | FLAIR | | | ADC | | | | | Location | | | | | | | No. of lesions | | Size | | | Mass effect | | | Age | | |
| DD | N | D | I | N | D | I | N | D | I | N | D | I | N | D | I | Y | N | CG | CW | dgw | BS | Ce | IV | EC | 1 | >1 | <1cm | 1-3cm | >3cm | M | N | L | C,<18 | A,18-60 | S,>60 |
| Abscess | 5 | 85 | 10 | 5 | 95 | - | 90 | 10 | - | 90 | 10 | - | 20 | 60 | 20 | 70 | 30 | 50 | 10 | 20 | 5 | 15 | 0 | 0 | 60 | 40 | 20 | 70 | 10 | 70 | 30 | 0 | 20 | 60 | 20 |
| Cerebritis | 0 | 50 | 50 | 30 | 70 | - | 90 | 10 | - | 99 | 1 | - | 10 | 80 | 10 | 5 | 95 | 60 | 0 | 20 | 5 | 15 | 0 | 0 | 90 | 10 | 10 | 70 | 20 | 20 | 80 | 0 | 20 | 60 | 20 |
| Cranio-pharyngioma | 10 | 20 | 70 | 80 | 20 | - | 90 | 10 | - | 90 | 10 | - | 70 | 20 | 10 | 20 | 80 | 0 | 0 | 10 | 10 | 0 | 10 | 70 | 99 | 1 | 10 | 80 | 10 | 20 | 80 | 0 | 80 | 10 | 10 |
| Glio-blastoma | 5 | 15 | 80 | 90 | 10 | - | 90 | 5 | 5 | 90 | 10 | - | 15 | 70 | 15 | 10 | 90 | 30 | 48 | 10 | 1 | 1 | 0 | 0 | 95 | 5 | 1 | 19 | 80 | 90 | 10 | 0 | 1 | 29 | 70 |
| Hematoma, intracerebral, subacute | 90 | 5 | 5 | 40 | 60 | - | 70 | 15 | 15 | 80 | 20 | - | 25 | 50 | 25 | 80 | 20 | 15 | 18 | 20 | 1 | 1 | 0 | 0 | 90 | 10 | 10 | 60 | 30 | 80 | 10 | 0 | 10 | 60 | 30 |
| Infarction, acute | 5 | 90 | 5 | 5 | 95 | - | 95 | 5 | - | 90 | 10 | - | 1 | 9 | 90 | 10 | 90 | 60 | 15 | 15 | 5 | 5 | 0 | 0 | 90 | 10 | 30 | 50 | 20 | 5 | 95 | 0 | 5 | 45 | 50 |
| Metastases, parenchymal, non-hemorrhagic | 10 | 30 | 60 | 95 | 5 | - | 70 | 20 | 10 | 90 | 10 | - | 70 | 20 | 10 | 5 | 95 | 50 | 20 | 20 | 5 | 15 | 0 | 0 | 20 | 80 | 20 | 70 | 10 | 70 | 30 | 0 | 5 | 60 | 35 |
| Multiple sclerosis | 1 | 80 | 19 | 25 | 75 | - | 80 | 20 | - | 90 | 10 | - | 15 | 80 | 5 | 5 | 95 | 5 | 70 | 10 | 90 | 10 | 0 | 0 | 5 | 95 | 60 | 37 | 3 | 2 | 93 | 5 | 5 | 90 | 5 |
| Rhomb-encephalitis | 5 | 70 | 25 | 1 | 99 | - | 90 | 10 | - | 80 | 20 | - | 15 | 80 | 5 | 5 | 95 | 0 | 0 | 5 | 5 | 5 | 0 | 0 | 99 | 1 | 5 | 80 | 15 | 3 | 97 | 0 | 20 | 60 | 20 |
| Toxoplasmosis | 5 | 35 | 60 | 95 | 5 | - | 90 | 10 | 2 | 90 | 10 | - | 20 | 70 | 10 | 5 | 95 | 20 | 10 | 60 | 5 | 5 | 0 | 0 | 70 | 30 | 5 | 85 | 10 | 40 | 60 | 0 | 10 | 89 | 1 |
| Xanthogranuloma, choroid plexus | 25 | 50 | 25 | 70 | 30 | - | 50 | 25 | 25 | 50 | 25 | 25 | 40 | 50 | 10 | 1 | 99 | 0 | 5 | 5 | 0 | 0 | 90 | 0 | 50 | 50 | 0 | 95 | 5 | 10 | 90 | 0 | 33 | 34 | 33 |
| Normal | 3 | 94 | 3 | 3 | 97 | - | 3 | 94 | 3 | 3 | 94 | 3 | 3 | 94 | 3 | 3 | 97 | 2 | 2 | 2 | 2 | 2 | 2 | 2 | 80 | 20 | 90 | 7 | 3 | 3 | 94 | 3 | 33 | 34 | 33 |

FIG. 5

SYSTEM AND METHOD FOR MEDICAL IMAGE ANALYSIS AND PROBABILISTIC DIAGNOSIS

CROSS-REFERENCE TO RELATED APPLICATIONS

This application is a National Stage Application filed under 35 U.S.C. 371 of International Application No. PCT/US2014/033715, filed Apr. 11, 2014, which claims the benefit of priority of U.S. Provisional Application Nos. 61/811,731, filed Apr. 13, 2013, and 61/812,112, filed Apr. 15, 2013, both titled "System and Method for Medical Image Analysis and Probabilistic Diagnosis," the contents of both of which are hereby incorporated by reference herein in their entireties, for all purposes.

GOVERNMENT RIGHTS

This invention was made with government support under grant numbers AG014971 and HC095178 awarded by National Institutes of Health. The government has certain rights in the invention.

TECHNICAL FIELD

The present invention relates to medical imaging and the interpretation of medical images.

BACKGROUND

Recently, there has been an explosive growth of digital imaging data, resulting in challenge and opportunity. Contemporary computational techniques can analyze immense amounts of complex data and are being incorporated into decision-support applications.

The annual $100 B medical imaging business is currently based on a high tech, 'picture taking' front end that feeds a low tech human back end that is responsible for creating the official end product—the Report. In this traditional process the extensive and remarkably sophisticated information contained in today's computer generated medical images from CT, MR, PET and real-time ultrasound systems ends up inadequately encapsulated in a radiologist's brief, subjective, qualitative report of less than a 100 words. The technological mismatch between contemporary digital imaging devices and analog human readers is not only operationally inefficient but also greatly limits the clinical value of the studies.

Medical image interpretation techniques have not kept up with medical image generation technology. Imaging in general and biomedical imaging in particular has two distinct elements—image production and image interpretation. Both are necessary for any practical application. While intimately related and mutually necessary, image production and interpretation are actually separate processes. Over the last 30 years there has been an 'explosion' of new and increasingly useful medical image production technology with CT, MRI, US, PET and SPECT now joining x-rays in exquisitely incorporating signals from most body parts into visually compelling images. Unfortunately, image interpretation, has not changed since Roentgen's time. The medical image interpreter is still the traditional human observer, albeit more highly trained and knowledgeable than the observer of 1900. While specialized human observers such as radiologists perform their interpretative tasks remarkably well, they by necessity use and are fundamentally limited by the human visual system. In addition, current radiology workflow is inefficient. The average time for a radiologist to view and report a standard radiographic study is 3 minutes, of which approximately 25% is dedicated to the mechanics of report generation. The administrative components necessary for report generation are not merely tedious, but are distinctly unpleasant, made even more so by current voice recognition (VR) systems.

All radiologists and other imaging specialists are intrinsically variable in their observations, insensitive to small signal changes, unappreciative of complex spatial patterns and are non-quantitative. As image acquisition technology improves, these human limitations increasingly constrain the useful information available from more refined image data. Medical images are now intrinsically digital, all being derived from computer processing. In contrast to human image analysis, computational results are invariable, sensitive to subtle signal changes imperceptible to the naked human eye (fMRI), reflective of very complex spatial patterns (Alzheimer Disease atrophy patterns) and intrinsically quantitative, allowing much more sophisticated statistical analysis. Computer analysis also offers the opportunity to reduce the costs of medical image analysis, having computers more economically and efficiently perform mundane interpretative tasks, leaving more demanding tasks for the more expensive specialized reader. However, while there are numerous biomedical image analysis computer algorithms, most work at a relatively leisurely pace, and have limited scope, operating in an ad hoc fashion on very narrowly defined tasks proscribed by specific research hypothesis.

Not perceiving an image finding is a major contributor to missed diagnosis, the most important clinical and medicolegal interpretative error. A long-recognized mechanism for decreasing missed findings is 'double reading.' Double reading involves two human observers viewing and interpreting the same image study. This method has been shown to decrease missed diagnosis. Unfortunately, the logistical demands and cost of double reading has prohibited its general use, except in some specific circumstances. Double reading of screening mammograms was the standard of care in Great Britain. This practice has now been updated by using mammographic CAD software to perform the 'second read.' In terms of sensitivity and specificity, the combination of a radiologist and CAD has been demonstrated in a large clinical trial to perform as well as two radiologists, but with quicker turn-around time and less expense. While this study demonstrates the concept of using computer image analysis to improve both the interpretative quality and efficiency of a single radiologist, the practice has failed to be adopted widely in radiologic practice.

There are limitation(s) in current software capabilities/approaches that prevent their broad use for medical image interpretation. Though the concept of obtaining diagnostic support from computer software is not new, early systems had limited clinical success due to immature software capabilities, hardware limitations, operational inefficiencies, and cost. While improvements in technology have enabled utilization in such fields as the interpretation of mammograms, screening mammography is a relatively unique interpretive task with very limited diagnostic choice and little urgency. These conditions can be met with 'niche' software and relatively primitive computational resources. To date there are no image analysis software tools that are robust enough to be applied broadly to medical image interpretation and able to operate within the acute care timeframe. Modern image analysis software remains very task specific (though SPM and various image analysis toolkits offer broader analytical capabilities), operationally demanding, and slow relative to the clinical environment.

There is a need for a systematic method and system of interpreting medical images that is efficient, inexpensive and minimizes human error.

SUMMARY

Methods for obtaining a probabilistic diagnosis of a patient are disclosed. In exemplary embodiments, such methods include the steps of scanning some or all of a patient to obtain a medical image; identifying one or more designated key features in the medical image; assigning discrete values to the one or more designated key features to form a patient scan key feature pattern; and transmitting the patient scan key feature pattern to a processor programmed to match the patient scan key feature pattern to one or more known disease-specific key feature patterns to create a probabilistic diagnosis and transmit the probabilistic diagnosis to a user. The key feature identification step can be performed by a human, by a computer program, or a combination of a human and a computer program. In some embodiments, the values assigned are quantitative, while in other embodiments, the values assigned can be semi-quantitative. In other embodiments, such methods include the steps of scanning some or all of a patient to obtain a medical image; and transmitting the medical image to a processor programmed to create a probabilistic diagnosis by: evaluating the medical image for one or more designated key features; assigning quantitative values to the one or more designated key features to form a patient scan key feature pattern; matching the patient scan key feature pattern to one or more known disease-specific key feature patterns to create a probabilistic diagnosis; and transmitting the probabilistic diagnosis to a user.

Systems for obtaining a probabilistic diagnosis of a patient are also disclosed. In exemplary embodiments, such systems include a medical imaging device that is capable of producing a medical image of some or all of a patient; and a processor programmed to create a probabilistic diagnosis by matching a patient scan key feature pattern comprising one or more quantitative or semi-quantitative values corresponding to designated key features extracted from the medical image to one or more known disease-specific key feature patterns and transmitting the probabilistic diagnosis to a user. The processor can be further programmed to extract one or more quantitative values corresponding to one or more designated key features from the medical image before matching the patient scan key feature pattern, such as by identifying one or more designated key features in a medical image and assigning quantitative values to the one or more designated key features to form a patient scan key feature pattern. In some embodiments, the values corresponding to key features are semi-quantitative rank ordered values. In other embodiments, the values corresponding to key features are quantitative.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. In the drawings:

FIG. 3A graphically depicts the steps of an embodiment of a method of the invention;

FIG. 5 illustrates an extracted subset of DDx disease lists with corresponding KF probabilities from a Brain Disease/KF table.

DETAILED DESCRIPTION OF ILLUSTRATIVE EMBODIMENTS

The present invention may be understood more readily by reference to the following description taken in connection with the accompanying Figures and Examples, all of which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer both to the features and methods of using systems for probabilistic diagnosis, as well as the systems themselves, and vice versa.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Finally, while an embodiment may be described as part of a series of steps or part of a more general structure, each said step may also be considered an independent embodiment in itself.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are described herein.

Figure 1:
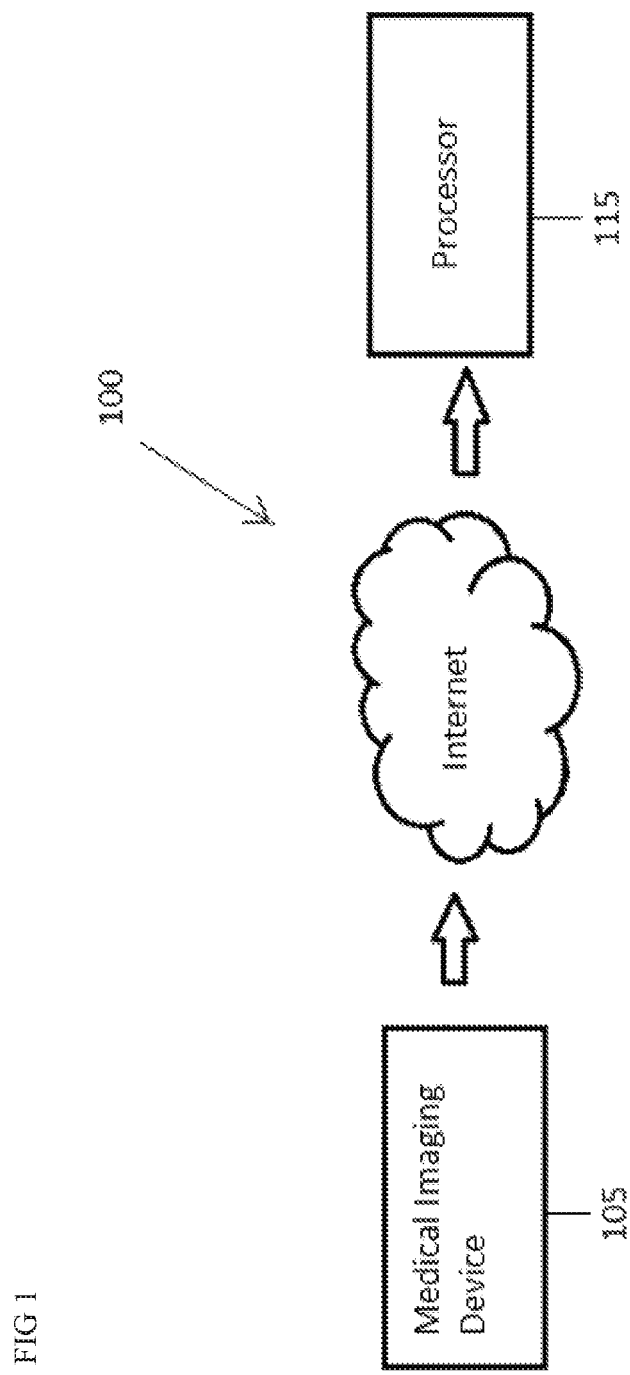
FIG. 1 illustrates schematically the elements of an embodiment of a system of the invention.

FIG. 1 illustrates a system of the invention (100) including a medical imaging device (105) that is capable of producing a medical image of some or all of a patient; and a processor (115) programmed to create a probabilistic diagnosis by matching a patient scan key feature pattern comprising one or more quantitative or semi-quantitative values corresponding to designated key features extracted from the medical image to one or more known disease-specific key feature patterns and transmitting the probabilistic diagnosis to a user. A probabilistic diagnosis is also referred to throughout as a differential diagnosis and can refer to one or more candidate diagnoses, each ranked by its likelihood. Suitable medical imaging devices (105) include any device that produces a visual image of some or all of a patient, including but not limited to, CT, MRI, US, PET, X-Ray, and SPECT. The processor can be further programmed to extract quantitative values corresponding to one or more designated key features from the medical image before matching the patient scan key feature pattern, such as by identifying one or more designated key features in a medical image and assigning quantitative values to the one or more designated key features to form a patient scan key feature pattern. Key features are aspects of a medical image that can be identified by the signal of the image, such as the brightness, space within the image, such as size, shape, and position, and changes over time between multiple images, such as stability. Patient scan key feature pattern refers to a group of one or more key features and the quantitative or semi-quantitative values assigned to the one or more key features. Known disease-specific key feature pattern refers to a group of one or more designated key features and corresponding probabilities that are associated with a specific disease. Throughout this disclosure, such a processor (115) that is programmed both to extract patient scan key feature patterns and to apply patient scan key feature patterns to one or more known disease-specific key feature patterns can be referred to as RadDx. In some embodiments a system of the invention can also include a Report Generator (RG) to convey the key features and/or diagnosis to a medical professional or the medical community. An RG can convey the key features and/or diagnosis in the form of a written or electronic report. A processor (115) comprising programming or programming on a processor that applies a patient scan key feature pattern to one or more known disease-specific key feature patterns is also referred to herein as an expert system (ES). In some embodiments, the system further includes a processor that can be programmed to perform the steps of: identifying one or more designated key features in a medical image and assigning quantitative values to the one or more designated key features. Transmission can include electronic transmission, such as over the internet or an intranet.

Figure 2:
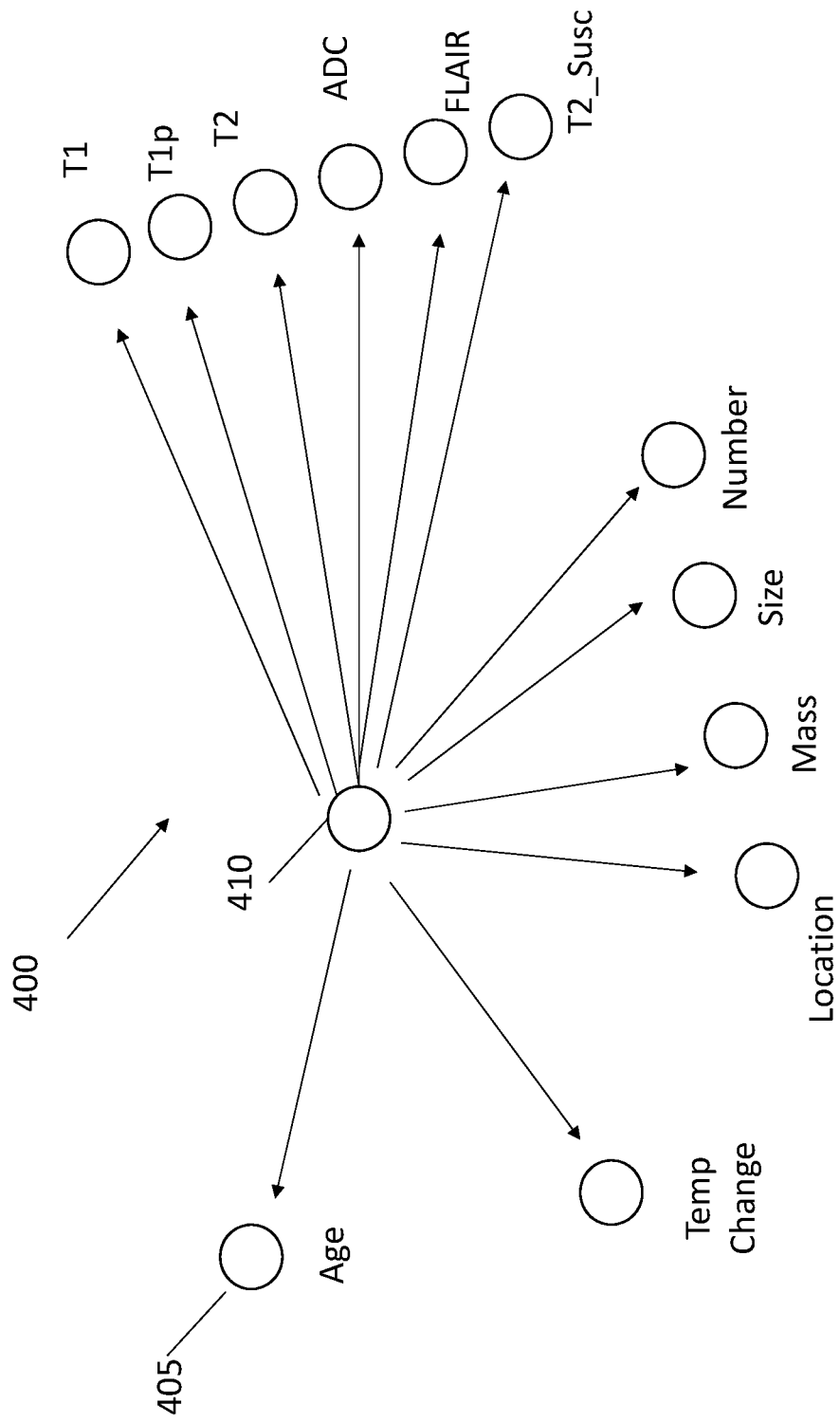
FIG. 2 illustrates an Expert System as instantiated in a Bayesian network.

A patient scan key feature pattern can be matched to a known disease-specific key feature pattern in a Bayesian network. FIG. 2 illustrates a portion of an example Bayesian network (400) according to the invention. The peripheral nodes (405) correspond to key features that relate to an individual patient scan, that is, the peripheral nodes represent the patient scan key feature pattern. The central node (410) corresponds to a known disease-specific key feature pattern including probabilities relating to each of the key features; FIG. 2 shows a key feature pattern for an abscess. An ES of the invention can be programmed to include known disease-specific key feature patterns of any number of known diseases. The ES can be programmed to match a patient scan key feature pattern to each of the programmed known disease-specific key feature patterns and to provide a probable diagnosis based on the matching.

A prototypical Bayesian expert system has been developed that takes input key features (KFs) detected in images and outputs a differential diagnosis (DDx) ranked by posterior probability. The methodology is based on the definition and extraction of key features (KFs) from the three intrinsic image domains: signal, space and time. These KFs, and appropriate clinical information, are fed to a Bayesian network Expert System (ES) that derives a clinical differential diagnosis (DDx). A Report Generator (RG) can incorporate the KFs into the "Findings" and DDx into the "Impression" components of a standard clinical report that may be incorporated as free text or defined fields in an electronic medical record (EMR). The algorithm is self-learning as it also generates a relational Knowledge Base of KFs and DDxs that can be linked to other components of the EMR for further scientific analysis and continual updating of the Bayesian ES. Such a system can include software that is applicable to any image type.

A clinical digital image analysis and reporting system is provided that can replace current report generation tools for medical imaging. The RadDx tool can operate in conjunction with a radiologist in the clinical environment and timeframe, rendering a penultimate report for review and verification by an appropriate clinician. Because of its added clinical value and operational efficiency, systems of the invention can be fully integrated with a radiologist so that the final report benefits from and reflects the unique contributions of the computer and human.

FIG. 3A illustrates a method including the steps of scanning (205) some or all of a patient to obtain a medical image; identifying (207) one or more designated key features in the medical image; assigning (210) discrete values to the one or more designated key features to form a key feature pattern; and transmitting (212) the patient scan key feature pattern to a processor (215) programmed to match the patient scan key feature pattern to one or more known disease-specific key feature patterns to create a probabilistic diagnosis; and transmit the probabilistic diagnosis to a user. The identifying step (207) can be performed by a human, by a computer program, or a combination of a human and a computer program. In the identifying step the key feature can be recognized and in the assigning step the key feature is given a discrete value. In some embodiments the values assigned are quantitative, while in other embodiments the values assigned can be semi-quantitative. Semi-quantitative values are discrete, and while semi-quantitative values need not be numeric, they can be ordinal such as rank ordered values, or categorical. The values assigned to the key features can be entered into a computer interface before transmitting (212) to an expert system. When the identifying and assigning steps are performed by a computer, the identifying and assigning steps can be performed simultaneously. Transmission can include electronic transmission, such as over the internet or an intranet.

Figure 3B:
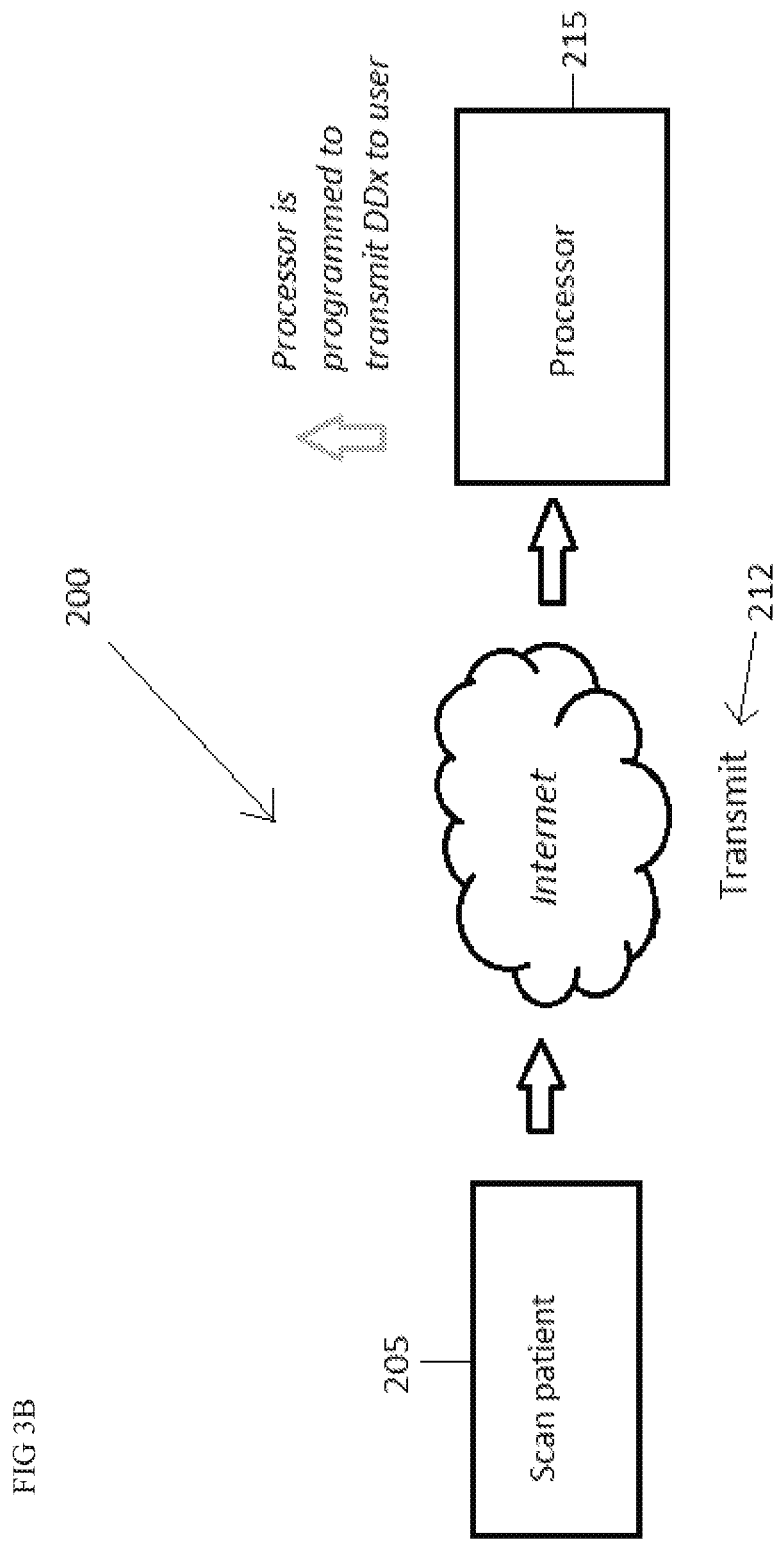
FIG. 3B graphically depicts the steps of another embodiment of a method of the invention.

FIG. 3B illustrates a method including the steps of scanning (205) some or all of a patient to obtain a medical image; and transmitting (212) the medical image to a processor programmed to create a probabilistic diagnosis by: identifying one or more designated key features in the medical image; assigning quantitative values to the one or more designated key features in the patient scan key feature pattern to form a patient scan key feature pattern; matching the patient scan key feature pattern to one or more known disease specific key feature patterns to create a probabilistic diagnosis; and transmitting the probabilistic diagnosis to a user. The identifying and assigning steps can be performed simultaneously. Transmission can include electronic transmission, such as over the internet or an intranet.

A method of interpreting a medical image has been developed that can result in efficient interpretation of a medical image with a consistent degree of accuracy. The generic image analysis process can be summarized as: 1) normalization of individual images to a common reference space; 2) deconstruction of image data into 3 intrinsic image domains—signal (brightness), space (size, shape, and position), and time (stability); 3) extraction of KFs from each domain; and 4) probabilistic matching of individual examination KFs to key feature based models of diseases.

Systems of the present invention can include a computer programmed to run algorithms capable of extracting KFs from a broad range of medical images across the three intrinsic image domains—signal, space, and time. A core theoretical innovation of the invention is the concept of generic image interpretation based on deconstructing and analyzing image data in these three intrinsic image domains and integrating it with a refined expert system, such as a Bayesian network that utilizes not only the image data, but other relevant non-image data contained in a contemporary electronic medical record (EMR) to yield a probabilistic differential diagnosis.

The invention includes a computer-enabled medical image interpretation process through software operating in a real-time clinical environment. The invention also includes a system that can include generalizable software for clinical image interpretation that can be used by radiologists as a "second read."

In accordance with another aspect of the invention, a computer can be used to perform image analysis tasks that humans simply cannot do. The computer's analytical capabilities allow reporting physicians to take more advantage of image data that is now below the threshold of human observation. For example, a high resolution, multi-modality MRI of the brain of a 70 year old male might be used to not only diagnose the mass of a glioblastoma, but also demonstrate the relationship of the lesion to the motor cortex and the subtle atrophy pattern of coincident Alzheimer Disease. The traditional radiologist currently contributes only the basic diagnosis, while the second two image findings of this case require contributions by the computer. Furthermore, the computer results are intrinsically quantitative and highly structured, both appropriate for modern EMR and information systems. The quantitative, structured results of computerized interpretation will allow more precise, direct communication of detailed image data, decrease practice variability due to ambiguity of qualitative verbal reports and allow evolving informatics tools to utilize discrete image data types for subsequent practice and outcomes analysis.

The proposed computerized image interpretation system can complement the valuable, but qualitative, human observer role of radiologists with more reliable scientific results from quantitative computational analysis. This progress is in keeping with the general incorporation of discrete data, computers, and modern informatics into medicine.

A 'real time' computer reporting system of 'reasonable cost' that creates reports of 'comparable quality' to human generated reports and decreases interpretive time 20% would immediately replace current report generating systems. If the system added quantitative results to current qualitative results, its practice and economic value would be greater. If the system improved diagnostic accuracy, it would become a practice requirement. Of course, 'real time,' 'reasonable cost,' and 'comparable quality' have to be defined. With current and projected decreases in professional reimbursements, the proposed system's elimination of the distasteful task of recording manual interpretations, and decreasing interpretative time by 25% would be of significant psychological and economic value.

In one embodiment, feature extraction software can be used for the quantitative analysis of brain MRI studies. Software can extract key image features from protocol-defined MRI examinations and quantitatively report them for subsequent statistical testing of study hypothesis. KFs extracted from multi-signal (FLAIR, PD, T1, T2, DTI, ASL and fMRI) MRI studies can include relative signal intensity (signal domain), volume, anatomic location (spatial domain) and change over time (temporal domain). Software can be modified to extract KFs defined by the clinical objectives of the user.

Software of the invention can take digital data in standard DICOM format from a Picture Archival System (PACS) archive such as the University of Pennsylvania Hospital System (UPHS) clinical PACS archive and render a structured report, including KFs and DDx. The analytical process involves two sequential steps: 1) KF extraction and 2) DDx generation, the latter based on the former. This task specific software is capable of classifying any pathological tissue in any organ. The algorithm deconstructs the data into the three intrinsic image domains: signal, space and time. KFs are embedded in and extracted from these domains. Each domain is analyzed separately, but in parallel. Analysis is voxel/lesion/organ based, with individual patient image metrics normalized and statistically compared to a reference population. Results for each domain's KFs are statistically summarized, i.e. Z score, which may then be classified into categorical numerical or verbal descriptors having arbitrary dynamic ranges of, for example, three (decreased, normal, increased) or seven ((−3, −2, −1, n, +1, +2, +3; normal, mild, moderately, severely increased/decreased). Training sets with reference distributions for each metric are derived from normal and clinical digital image archives. The extracted KFs from an individual patient are then fed into the expert system (ES) that best matches a patient image KFs to a library of specific disease KFs. The ES outputs a DDx in rank order of likelihood for this patient, based on the image data and any other clinical data used in the predictive model. Finally, the Report Generator (RG) incorporates the KFs and DDx into the "Findings" and "Impression" components of a standardized radiological report. The KFs and DDx are also added to a continually updated, relational Knowledge Base that can be used for additional purposes, including workflow management, outcomes analysis and statistical validation of the image analysis software.

Key Feature Extraction Tool

Figure 4:
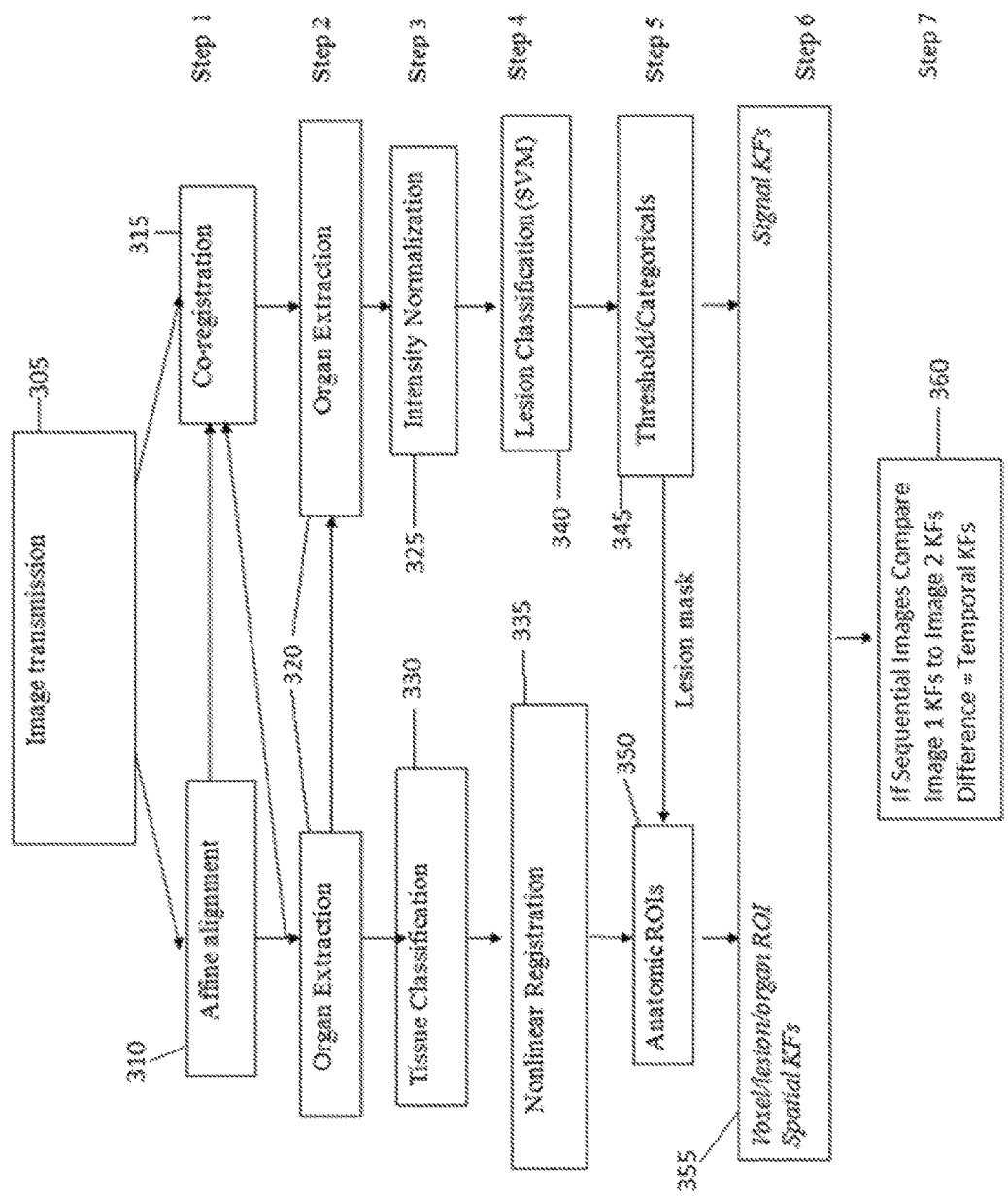
FIG. 4 illustrates a flowchart of the method by which a key feature extraction tool can be programmed to operate.

FIG. 4 illustrates a flowchart of the method by which a key feature extraction tool can be programmed to operate. The flowchart of FIG. 3 is also representative of a process for performing a step of evaluating the key features in a medical image in a method of the invention.

As shown in FIG. 4, Step 1 involves preparatory intra patient study operations including affine alignment (310) and co-registration of study images (315) following image transmission (305). Step 2 explicitly extracts (320) each major organ to be evaluated. For example, the Brain Extraction Tool (BET) can be applied for brain analysis. Step 3 involves signal and spatial normalization (325) of an individual patient image. The distribution of signals from a given examination (x-ray, CT, MRI, etc. of a particular organ) is normalized to the corresponding distribution of signal intensities of a reference population. A tissue segmentation tool can be used to subdivide the population signal distribution into major tissue types of the respective organ (i.e., bone, water, fat, etc.) (330). These tissue labels can be assigned to each patient image voxel, each of which now has a signal and tissue label.

Still referring to FIG. 4, for step 4 of spatial KF analysis, the tissue-labeled, organ image can be non-linearly registered (335) with a registration algorithm to a corresponding anatomic template, which is probabilistic and population based. Patient images are now in comparable signal (brightness) and spatial (anatomic) reference spaces. Each voxel has normalized signal intensity and an anatomic label. The spatial registration process not only anatomically labels the voxels, but also quantitatively defines the spatial variation of each voxel from its population based norm, allowing for explicit spatial analysis. In the initial tissue classification step, individual voxels are assigned to an organ and classified as normal or abnormal in terms of signal intensity, the later state defined as 'lesion' (340). Spatial domain analysis can be performed at the organ, lesion, or voxel level. Using morphometric tools, each organ, or lesion, can be described by traditional spatial descriptors, such as number, size, shape and position. This analytical step might output, for example, "the ventricles and sulci are moderately enlarged."

For step 4 of signal KF analysis, the globally normalized signal intensity of each voxel can be compared to the distribution of signals from the spatially corresponding voxel in the reference population using a non-linear pattern classifier constructed from a training set using, for example, a support vector machine (SVM) tool (345). The SVM can calculate an attribute vector (AV) for each voxel, defined as:

$$F(v) = \{I(t_m) | t_m \in \Omega(v_m), m \in S_1, S_2 \ldots S_n\}$$

It can then calculate distances in Hilbert space from predefined 'normal' tissue. The AV can have one or more signal components. In the case of MRI, these might include PD, T2 and pre and post contrast T1. The output of SVM is a scalar measure of abnormality which is converted to any categorical scale through optimal thresholds. Each voxel in a patient image can be classified as normal or abnormally increased or decreased using, for example, the 3 scale classifier. Once the patient image is anatomically labeled, the location(s) of abnormal signal intensity(s) can be anatomically defined (350). For example, from an x-ray CT scan this analytical step might output, "markedly increased signal intensity (radiodensity) in the right caudate nucleus."

Temporal domain KF analysis (360) in Step 7 is driven by change over time and requires at least two sets of images from the same patient made at different times, commonly before and after treatment. For this analysis, the preparatory step includes the spatial registration of the second study to the same anatomic template used for the first study. A difference operator defines voxels in the second image that have changed in signal intensity or spatial location from the first exam. Temporal changes are reported as: no change, progressive (differing more from the normal template than the first exam) or resolving (more similar to the normal template than the first exam). This step might output, for example, "ventricles and sulci have decreased in size, as compared to the previous study."

The above analytical steps yield signal, spatial and temporal KFs from a patient's imaging study (355). These KFs may be represented in a multidimensional table with each organ or lesion having signal, spatial (and temporal) KFs and sent as such to the Expert System and Knowledge Base.

Differential Diagnosis Expert System (ES)

For development of a DDx, the KFs of a patient study are best matched to a library of specific disease KFs by the ES using a Bayesian network designed to output DDx based on predefined KFs. KFs can be extracted by human observers (radiologists), specific software, or both. FIG. 5 illustrates an extracted subset of a DDx disease list with corresponding KF tables from a Brain MRI Disease/KF table. In this table there are 6 MRI signal, 10 spatial and one time image KF plus 1 non-image based predictor (age).

For a simplistic operational example, the ES can take the KFs of a theoretical 'Unknown' case and enter them as predictive nodes in the Bayesian network (FIG. 2) that contains the Disease outcome nodes and probability estimates of the causal connections. The program will perform the probabilistic calculations resulting in the DDx: 1) Rhombencephalitis (P=0.7), 2) Cerebritis (P=0.2).

The ES can be based on the probabilistic underpinnings of Bayesian networks with KFs and DDx being represented by 'state-of-affair' nodes linked to the disease specific nodes by relational connections. In one embodiment, a brain ES program can have approximately 120 diseases, 20 image KFs and 4 initial non-image predictors.

Report Generator (RG)

An RG based on embedding KFs into a commercial radiology reporting application can be used for result reporting. This tool can incorporate KFs into the Findings section of a standard radiology report. The RG can also create a relational database containing the discrete KF and DDx results. In one embodiment, RG can require human KF extraction and data entry. In another embodiment, the RG can accept comparable computer-generated KFs, or a combination of human KF extraction and entry and computer KF extraction and entry. Likewise, the DDx within the Impression section of the report can be human generated, or can accept the ES generated DDx. The RG can use standard terms from the RADLEX and SNOMED lexicons for all study variables.

The final output of the ES can be a standardized text report that includes the KFs and the final DDx, with statistical likelihood. In addition, the KFs and DDx of each case are added to the evolving Knowledge Base that is used for a continual updating of the Bayesian ES. Operational and technical factors related to the image may also be added to the Knowledge Base for other operations such as workflow management, regulatory documentation, Quality Control and outcomes analysis.

Integration and Validation of the Software Components

Result evaluation of software can be based on sensitivity/specificity and ROC analysis of computer generated KFs and DDx as compared to clinical or pathologically defined ground truth or radiologists' interpretations of the same cases. Computer and radiologist results can be categorical in terms of KFs, while DDx can be treated as discrete, rank ordered variables. The feature extraction software can be programmed to output KFs as, for example, 3 or 7 scale categoricals. The KFs can be relatively limited in number (1-6 signal; 2 spatial; 1 temporal for each modality), but there can be many more possible DDx variables (for example, approximately 120 in the current Brain Disease table). In order to have comparable human derived KFs, a novel radiology reporting tool has been developed. Custom templates include fields that correspond to the KFs generated by the computer and used in the DDx ES. Hence, this unique reporting tool allows radiologists to generate comparable, discrete predictive (KFs) and outcome (DDx) variables with minimal disruption of their routine workflow. Software can be used to extract these variables from clinical reports. These same clinical cases can then be analyzed by the computer analysis software.

For these validation analyses, an evaluation set of pathologically confirmed cases can be interpreted by radiologists and the computer. For example, the cases can be reflective of cases seen in these radiologists' practice. Cases can be randomly selected by first searching for matching diagnosis corresponding to the selected test diagnoses. These candidate cases can then be reviewed by a radiologist for confirmation of diagnosis and technical quality of the imaging studies, which must be appropriate for the KF software. In an example validation procedure, for each task, the evaluation set can consist of a defined number of disease conditions, each with representative patient studies plus normal cases. Using the RG, each radiologist can interpret the full evaluation set one or more times. The computer can also be used to interpret the evaluation set any number of times, such as twice. These readings can result in individual image interpretations that can be used for inter and intra human, inter human/computer, and intra computer reader analysis.

The human and computer results can be statistically tested for comparability. Univariate analysis of the agreement ratings over the human and computer report pairs can be calculated. Kappa and weighted kappa statistics as well as ROC curves can be computed for the entire sample.

EXAMPLES

The following examples, while illustrative of an individual embodiment, are not intended to limit the scope of the described invention, and the reader should not interpret it in this way.

Example 1

A prototype neuroradiological decision-support application was developed and evaluated using a small set of clinical neuroradiological MR examinations. Readers selected similar KF values regardless of experience level. There was excellent agreement between each reader's most likely diagnosis and the known diagnosis.

Materials and Methods: Eleven neuroradiological entities (abscess, cerebritis, craniopharyngioma, glioblastoma, hematoma, infarct, metastasis, multiple sclerosis, rhombencephalitis, toxoplasmosis, xanthogranuloma) and normal, were evaluated by a senior neuroradiologist to identify characteristic and idealized imaging KFs and approximate conditional probabilities of these features. These features and probabilities were used to build a Bayesian expert system for differential diagnosis. Two neuroradiologists selected a test set of 100 diagnosis-proven MR examinations from the University of Pennsylvania PACS: 6 for each entity. Three diagnosis-blind readers—attending neuroradiologist, neuroradiology fellow and PGY-3 radiology resident—reported the KFs and their rank ordered DDx after reviewing each case. Each reader's KFs were entered into the model, obtaining a posterior probability ranked DDx list for each case-reader combination. The reader's observed KFs were compared to each other and to the ideal disease features, and the readers' DDx were compared to those of the model and to each other. The DDx lists were also compared to the clinically proven diagnosis. Percentage agreement, kappa statistics, and ROC analysis were used to evaluate human and computer reader performance.

Results: For individual extracted KFs, there was moderate to excellent agreement between the different human readers (57-91%), which was similar to agreement between individual reader KFs and the idealized KFs for the various diseases (42-94%). Inter-reader agreement for each feature was similar to agreement between readers and the model system KFs. The model, using ideal cases (i.e., cases with "classic" features, as determined by a senior neuroradiologist), was in 100% agreement with the known diagnosis. These results indicate that the KFs upon which the model system was based are concordant with actual clinical cases. The primary diagnoses of the human readers versus the proven diagnoses showed percent agreement of 77-92% and K=0.74-0.91. ROC analysis of DDx for human readers and model output diagnoses based on human extracted KFs all demonstrated excellent performance, with humans (AUC 0.91-0.93) performing only slightly better than the model (AUC 0.66-0.82).

Example 2

An initial model Bayesian network Expert System was built based upon the opinion of one expert neuroradiologist (RNB) and used to generate a differential diagnosis from key features (KFs) extracted from representative cases by 3 blinded readers of varying experience. This network, defined as M1P1, integrates data extracted from brain MRI studies using pre-defined conditional probabilities (CPs) to output posterior probability for eleven distinct neuroradiologic entities and normal. To improve the performance of a computer aided differential diagnosis system for neuroradiology, expert consensus via a modified Delphi method and a data driven method are compared. The goal of this example was to improve performance of the Bayesian ES model by altering the model's conditional probabilities.

Materials and Methods. Two methods were used to modify the CPs: expert consensus and data-driven. For the former, a modified Delphi method was used. Three neuroradiology specialists independently generated CPs for the network, which were then shared, reviewed and independently revised. After 3 rounds, the reader's tables were averaged and input to the model, defined as M1P2. For the data driven approach, the conditional probabilities for each state were calculated from the KFs extracted by the three diagnosis blind case readers and input to the model, defined as M1P3. The Bayesian ES model network structure was not changed.

Results. The Delphi consensus resulted in a change of greater than 10% compared to the single expert model for 90 (22%) and in greater than 25% for 29 (7%) of 408 distinct CPs. The data-driven model changed 41% of CPs by over 10% and 18% of CPs by 25% or more. The same case KF data was run through the single expert (M1P1), consensus (M1P2), and data-driven models (M1P3), which were evaluated with kappa statistic and ROC analysis. The radiologist's self-generated diagnosis (Rad-DDx) and M1P3 had the highest AUC while M1P1 had the lowest. Compared to Rad-DDx, M1P1 showed significant difference (p<0.01) while M1P2 and M1P3 did not. Partial ROC curve analysis showed significant difference between M1P3 and M1P1 (p=0.026) and a trend towards significance between M1P2 and M1P1 (p=0.09) while M1P2 and M1P3 did not differ.

Delphi expert consensus, and data-driven analysis resulted in changes to CPs underlying a Bayesian ES system for neuroradiologic diagnoses. Expert consensus, which can reduce personal and recall bias, and a data driven method, limited by the size and representativeness of the sample it was derived from, can improve performance of a prototype differential diagnosis system for Neuroradiology.

It is to be understood that while the invention has been described in conjunction with the preferred specific embodiments thereof, that the foregoing description and the examples that follow are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains. In addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

What is claimed:

1. A method for obtaining a probabilistic diagnosis of a patient, the method comprising:
    a medical imaging device scanning some or all of a patient to obtain a medical image;
    identifying one or more designated key features in the medical image;
    assigning discrete values to the one or more designated key features in the medical image to form a patient scan key feature pattern;
    transmitting the patient scan key feature pattern to a processor;
    the processor implementing an expert system to match the patient scan key feature pattern to one or more known disease specific key feature patterns to create a probabilistic diagnosis; and
    the processor transmitting the probabilistic diagnosis to a user.

2. The method according to claim 1, wherein the identifying step is performed by a human.

3. The method according to claim 1, wherein the identifying step is performed by a computer.

4. The method according to claim 1, wherein the values assigned to key features are quantitative.

5. The method according to claim 1, wherein the values assigned to key features are semi-quantitative.

6. A method for obtaining a probabilistic diagnosis of a patient, the method comprising:
    a medical imaging device scanning some or all of a patient to obtain a medical image;
    transmitting the medical image to a processor programmed to create a probabilistic diagnosis by:
    identifying one or more designated key features in the medical image;
    assigning quantitative values to the one or more designated key features in the medical image to form a patient scan key feature pattern;
    implementing an expert system that matches the patient scan key feature pattern to one or more known disease specific key feature patterns to create a probabilistic diagnosis; and
    transmitting the probabilistic diagnosis to a user.

7. A system for obtaining a probabilistic diagnosis of a patient, the system comprising:
    a medical imaging device adapted to produce a medical image of some or all of a patient; and
    a processor that implements an expert system to create a probabilistic diagnosis by matching a patient scan key feature pattern comprising one or more quantitative or semi-quantitative values corresponding to designated key features extracted from the medical image to one or more known disease-specific key feature patterns and transmitting the probabilistic diagnosis to a user.

8. The system according to claim 7, wherein the expert system creates a probabilistic diagnosis by extracting the one or more quantitative or semi-quantitative values corresponding to designated key features from the medical image before matching the patient scan key feature pattern.

9. The system according to claim 8, wherein the processor is programmed to extract quantitative values corresponding to one or more designated key features by:
    identifying one or more designated key features in the medical image; and
    assigning quantitative values to the one or more designated key features to form a patient scan key feature pattern.

10. The system according to claim 7, wherein the values corresponding to the key features are semi-quantitative rank ordered values.

11. The system according to claim 7, wherein the values corresponding to designated key features are quantitative.

12. The system according to claim 7, wherein the medical imaging device produces the medical image as a digital image in DICOM format.

13. The system according to claim 7, wherein the expert system comprises a Bayesian network.

14. The system according to claim 7, wherein the processor implements a report generator that transmits the probabilistic diagnosis to the user.

15. The system according to claim 7, wherein the patient scan key feature pattern is created by deconstructing the medical image into a signal domain, a space domain, and a time domain, and the processor implements an algorithm to extract key features from the signal domain, the space domain, and the time domain.

16. The system according to claim 15, wherein the expert system probabilistically matches key features extracted from the signal domain, the space domain, and the time domain with the one or more known disease-specific key feature patterns.

17. The system according to claim 15, wherein the processor analyzes each domain separately and in parallel and statistically summarizes the key features of each domain into a Z score that is classified into categorical numerical or verbal descriptors having arbitrary dynamic ranges.

18. The system according to claim 7, wherein the processor implements a tissue segmentation tool that subdivides the medical image into major tissue types of respective organs in the medical image.

* * * * *